Figure 1:
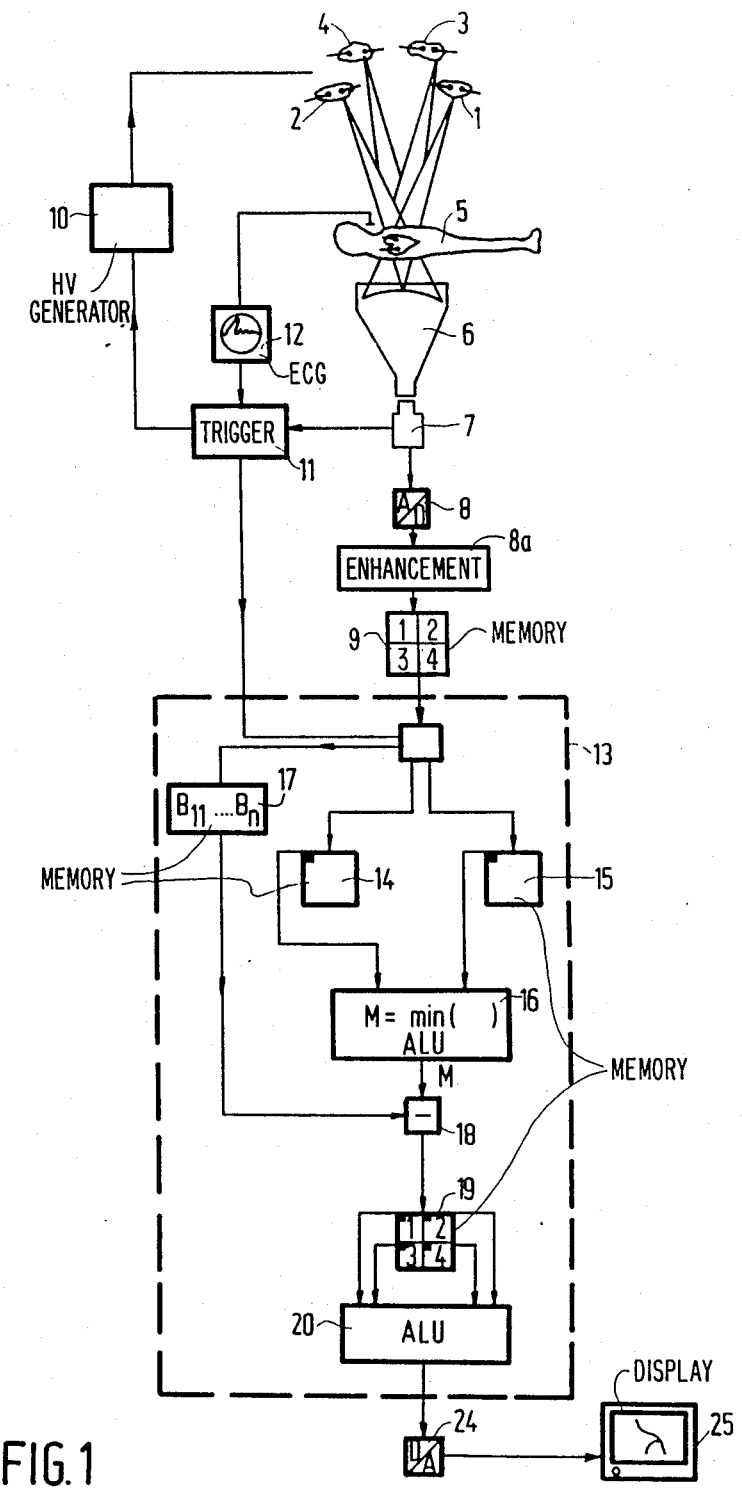

United States Patent [19] [11] Patent Number: 4,853,947
Haaker et al. [45] Date of Patent: Aug. 1, 1989

[54] METHOD OF GENERATING AN X-RAY LAYER IMAGE OF AN EXAMINATION ZONE, AND DEVICE FOR PERFORMING THE METHOD

[75] Inventors: Paul R. Haaker, Hamburg; Erhard P. A. Klotz, Halstenbek; Reiner H. Koppe, Hamburg; Rolf E. Linde, Haseldorf, all of Fed. Rep. of Germany

[73] Assignee: U.S. Phillips Corporation, New York, N.Y.

[21] Appl. No.: 99,569

[22] Filed: Sep. 22, 1987

[30] Foreign Application Priority Data

Sep. 26, 1986 [DE] Fed. Rep. of Germany ....... 3632833

[51] Int. Cl.$^4$ .............................................. H05G 1/64
[52] U.S. Cl. ......................................... 378/99; 378/2; 378/22; 378/23; 358/111
[58] Field of Search .......................... 378/22, 23, 99, 2; 358/111

[56] References Cited

U.S. PATENT DOCUMENTS

| 4,433,428 | 2/1984 | Haendle et al. | 378/99 |
| 4,436,095 | 3/1984 | Kruger | 378/99 |
| 4,630,296 | 12/1986 | Haaker et al. | 378/23 |
| 4,633,307 | 12/1986 | Honda | 358/111 |
| 4,644,575 | 2/1987 | Kruger et al. | 378/99 |
| 4,672,651 | 6/1987 | Horiba et al. | 378/22 |
| 4,698,671 | 10/1987 | Garcia | 378/99 |

Primary Examiner—Craig E. Church
Assistant Examiner—John C. Freeman
Attorney, Agent, or Firm—Jack E. Haken

[57] ABSTRACT

The invention relates to a method of generating a layer image from a plurality of single images, the image processing errors which locally occur in the single images being substantially eliminated in the layer image. To this end, the image values for the individual layer image points are formed by that image value of the image points geometrically situated with the layer image point which corresponds to the next to the lowest absorption value.

5 Claims, 2 Drawing Sheets

METHOD OF GENERATING AN X-RAY LAYER IMAGE OF AN EXAMINATION ZONE, AND DEVICE FOR PERFORMING THE METHOD

The invention relates to a method of generating an X-ray layer image of an examination zone by means of single images which are associated with different perspectives of the examination zone and for the image points of which there is stored a respective image value, each image value of a layer image point being formed by one of the image values of the image points of the single images geometrically associated with the respective layer image point, and also relates to a device for performing the method.

A method and device of this kind are known from DE-OS No. 32 37 572. The known device comprises four X-ray sources which form four separate single images of an examination zone to be irradiated. The single images are subdivided into a plurality of preferably square zones which have finite dimensions and which are referred to hereinafter as image points, the term "layer image point" being used to denote a corresponding zone in the layer image formed from the single images. For each image point of a single image the associated image value is stored in a storage device, said image value being a measure of the absorption or transmission of the examination zone in the respective image point. The image value which is thus assigned to a layer image point is derived from the image points which are geometrically associated with the layer image point. In the X-ray image wherefrom the relevant single image is formed, these image points are situated on the connecting line between the layer image point and the various X-ray sources.

According to the known method, preferably being used for generating layer images of the coronary vessels whose arteries are filled with a contrast medium, that image value of the image points of the single images geometrically associated with a layer image point which corresponds to the lowest absorption is each time assigned to the respective layer image point. The aim is to ensure that absorbing structures outside the layer do not cause any artefacts, or only minor artefacts, in the image of this layer.

The results of the known method are satisfactory for as long as the single images are not formed by an image processing method which produces "diluted" images, i.e. images which contain, in front of a more or less uniform background, important details (for medical or technical diagnosis) with image values which deviate significantly from the background in zones which are small in comparison with the overall image zone.

Diluted images of this kind can occur, for example when the single images are formed by means of a subtraction method where an X-ray image of a zone without contrast medium (mask image) is subtracted, each time for different perspectives, from an X-ray image of the same zone of the coronary vessels filled with a contrast medium ("filled" exposure); this mask image merely represents the background and can also be synthetically derived from a filled image, as described in DE-OS 35 14 683. The single image then formed contains hardly any skeleton and tissue structures and only shows the vessels filled with the contrast medium, the associated image values deviating distinctly from the image values of the background.

A diluted image also occurs when X-ray images are subjected to a pattern enhancement method. A pattern enhancement method of this kind can be used, for example to expose gas inclusions (shrinkholes) in X-ray images of cast components, said inclusions being hardly distinct from their environment in the non-processed X-ray image. This can be realized, for example by comparing each image value with a threshold value and by replacing it by a first value (characteristic recognized) or second value (characteristic not recognized), depending on whether it is larger or smaller than the threshold value.

Common aspects of both methods are that in the single images the details which are important for the diagnosis (vessels, shrinkholes) occupy only a comparatively small part of the total surface area of a single image and that the image values in the relevant image points are substantially distinct from those of the background. However, whilst in the first case the absorption of the details important for the diagnosis is higher than that of the environment, the absorption in the second case is lower (the transmission is greater) than in the environments. When the known method is applied to such single images, artefacts can occur in the layer image.

It is an object of the present invention to provide a method of the kind said forth so that the artefacts are further suppressed in the case of such "diluted" single images.

This object is achieved in that each time the image value which corresponds to the next to the lowest transmission or absorption value is used as the image value for the layer image point.

The invention is based on the following considerations.

During the formation of the single images errors may occur in that an image value which corresponds to the background is assigned to a detail which is important for the diagnosis. For example, when the mask image which is formed from a number of filled exposures and which is to be subtracted therefrom, erroneously assigns an image value which corresponds to a detail which is important for the diagnosis (vessel) to one of the image points of a single image in the subtraction method in accordance with DE-OS No. 35 14 683, this error will become manifest in that this vessel point will not appear in the single image formed by subtraction, so that the image value for this image point corresponds to an absorption which is substantially lower than in the absence of this processing error. In the known method, for the layer image point with which said vessel image point having the incorrect image value is geometrically associated, exactly this incorrect image value would be formed during the formation of the layer image from the single images because it corresponds to the lowest absorption; thus, whenever a vessel image point appears as a background image point during the formation of an arbitrary single image by subtraction of a mask image from a filled image, this error will be transferred to the layer image derived from the relevant single image and further single images.

The invention utilizes the fact that these image errors in the single images are not correlated, i.e. usually only one of the image values of the image points of the single images geometrically assigned to a layer image point contains the described error. Because the image value corresponding to the next to the lowest absorption value is used in accordance with the invention, the described error no longer has an effect on the determination of the image value of a layer image point, so that usually it does not appear in the layer image.

The errors in the single images which are caused by the fact that a (low-absorption) background image point appears as a (high-absorption vessel image point upon subtraction are also suppressed because the image value of this image point corresponds to the highest absorption so that it is not used for forming the image value for a layer image point. The artefacts in the layer image which are caused by absorbing structures outside the layer are also substantially suppressed.

The invention offers a similar suppression of artefacts also when the single images used for forming a layer image are the product of a pattern enhancement method.

A device for performing the method in accordance with the invention is characterized in that it comprises a plurality of radiation sources for forming X-ray images of the examination zone from different perspectives, means for processing the X-ray images so as to form single images, a storage device for storing the image values of the single images, and means for determining that image value of the image points geometrically associated with a layer image point which corresponds to the next to the lowest absorption or transmission value.

Figure 2:
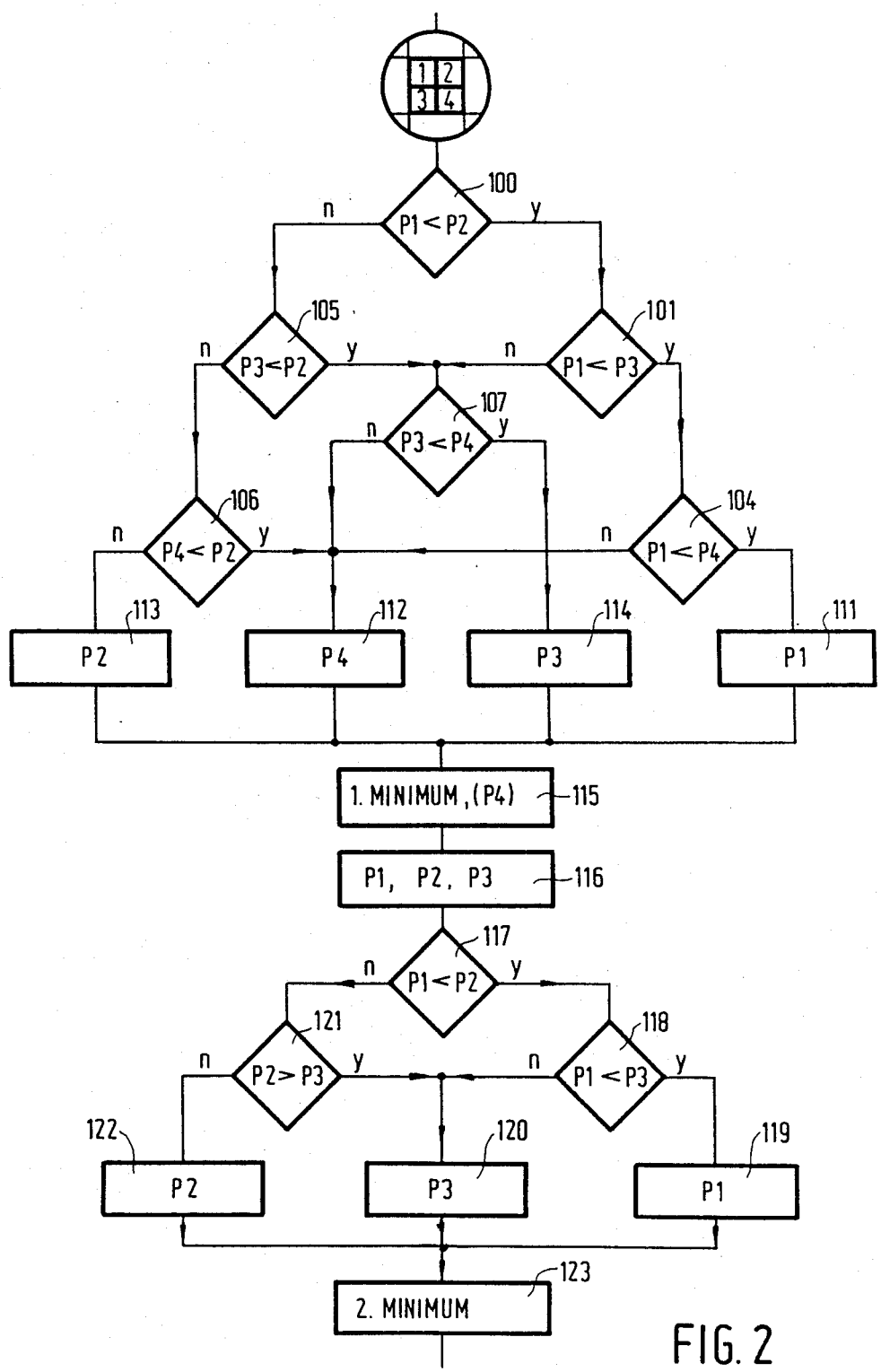

The invention will be described in detail hereinafter with reference to the drawing. Therein:

FIG. 1 shows diagrammatically a device for performing the method in accordance with the invention, and FIG. 2 shows a flowchart for determining the image value of a layer image point.

FIG. 1 shows four X-ray sources 1, 2, 3 and 4 which are arranged at the four corners of a square and whose beams are directed onto an examination zone in which the coronary vessels filled with a contrast medium of a patient 5 are situated. An X-ray image intensifier 6 converts the X-ray shadow images generated by the X-ray tubes 1 . . . 4 into visible images. Using a television camera 7, the visible images are converted into electric signals which are digitized by an analog-to-digital converter 8 for storage in a memory 9. If desired, the image features can be enhanced, for example by the threshold method described above, in an enhancement module 8a. The X-ray tubes 1 . . . 4 are simultaneously switched on by a high voltage generator 10 which is controlled by a trigger module 11 which derives its trigger signals from an electro cardiogram which is supplied by an ECG apparatus 12 connected to the patient 5. The X-ray sources 1 . . . 4 can thus be activated in defined phases of the cardiac cycle.

Activation takes place n times in different phases of the cardiac cycle, so that for each X-ray source 1 . . . 4 a sequence of n X-ray images B11 . . . B1n, . . . , B41 . . . B4n which depict the examination zone in different phases of the cardiac cycle are stored in the memory 9. Images of layers having a predetermined position are calculated for different phases of the cardiac cycle from the images stored by means of an arithmetic device 13. Via a digital-to-analog converter 24, these images are applied to a suitable image display device 25, for example a monitor. The calculation of the layer images is performed in two phases. During the first phase single images are calculated from the X-ray images stored. During the second phase, at least one layer image is calculated from four single images which show the coronary vessels each time in the same phase of the cardiac cycle but from different perspectives. The calculation of the single images is performed separately for each x-ray source as follows.

From the sequence of X-ray images of an X-ray source, for example the X-ray images B11 . . . B1n of the X-ray source 1, some images are selected which show the coronary vessels in distinct phases of motion. Initially two of these images are loaded into the memories 14 and 15. A first arithmetic and logic unit 16 compares the two images one image point after the other and each time stores that image point which corresponds to the lowest absorption. The image thus formed is loaded into one of the memories 14 and 15 and is compared in its turn with the next one of the selected images of the series. Ultimately, an image is obtained whose image values correspond to the minimum values of the absorption in the selected images.

Because a noticeable contrast is present between the coronary vessels and the background in the X-ray images and because the coronary vessels move in front of the background which is assumed to be stationary and uncover the background in individual phases, that is to say in individual images of the selected images, a minimum value of the absorption occurs for each image point whenever this image point in the selected X-ray images has not been obscured at least once by a moving coronary vessel. The image value for this image point thus corresponds to the background and the image thus formed, therefore, shows substantially only the background and no longer coronary vessels. This image can be used as a mask image M which is subtracted in the subtraction circuit 18 from the X-ray images B11 . . . B1n of the series loaded into the memory 17. Thus, the series of X-ray images is converted into a series of single images which show essentially only the vessels, while the background is suppressed, because the X-ray images contain the vessels as well as the background and the mask image subtracted therefrom contains only the background. This method is described in detail in German Patent Application No. P 35 14 683 and is repeated for the series B21 . . . B2n, . . . , B41 . . . B4n of the other X-ray sources 2 . . . 4, so that at the end of the procedure four series of single images (one for each X-ray tube) are available. In order to form a layer image for a given cardiac phase, the four single images of the four series associated with the relevant cardiac phase are loaded into a memory 19 and, as described in DE-OS No. 32 37 572, those image points are determined which are associated with the same layer image point.

If no errors were present in the selected single images, the image value corresponding to the lowest absorption would at least approximately correspond to the image value of the layer image point as described in detail in DE-OS No. 32 37 572. However, it may occur that in all X-ray images selected for forming the mask image one or more image points are obscured by vessels. Therefore, these image points are taken up in the mask image. The image values for these image points are substantially equal to the image values in the non-processed X-ray image of the series, so that they compensate for one another after subtraction and the single image produced for this image point by subtraction has an image value which correspons to a minimum absorption. If that image value of the geometrically associated image point which corresponds to the lowest absorption were each time used as the image value of a layer image point, the incorrect image value of this image point would form the image value of the spatially associated layer image point, i.e. the layer image would not show a vessel in this image point, even when the image values frm the other single images would correspond to a vessel for this image point.

It has been found, however, that the described errors do not occur in a spatially correlated manner, i.e. the other images will generally not show the same error in the image points associated with the same layer image point. Therefore, when that image value of the geometrically associated image points which corresponds to the next to the lowest absorption value is selected as the image value for the layer image point from the four single images, the relevant layer image point will represent a vessel when the vessel is present within the layer imaged, i.e. in that case an error contained in a single image will not be transferred to the layer image formed therefrom.

The method whereby, in a second arithmetic and logic unit 20, the image value can be determined with corresponds to the next to the lowest absorption valve will be described in detail with reference to the flowchart shown in FIG. 2. It is assumed that the four image values P1, P2, P3, P4 of the image points of the single images which are geometrically associated with a layer image point are available in stored form. First, P1 and P2 are compared (block 100). If P1 is smaller than P2, a branch operation takes place to the block 101 in which P1 is compared with P3. When P1 is again smaller than P3, a branch operation takes place to block 104 in which P1 is compared with P4. If P1 is smaller than P4, P1 is the smallest value (block 111); otherwise, P4 is the smallest value (block 112).

If P1 is not smaller than P2, a barnch operation takes place to block 105 in which P2 and P3 are compared. If P3 is larger than P2, a branch takes place to block 106 in which P4 and P2 are compared. If P4 is again larger than P2, P2 is the smallest image value (block 113); otherwise, P4 is the smallest value again.

When block 105 reveals that P3 is smaller than P2 or when the comparison in block 101 reveals that P1 is not smaller than P3, a branch operation takes place to the block 107 in which P3 and P4 are compared. Depending on the result of this comparison, either P3 (block 114) or P4 is the smallest image value. Thus, when one of the blocks 111 ... 114 is reached, it is known which image value is the smallest or corresponds to the lowest absorption (block 115). For example, when this is the image value P4, only the three image values P1, P2, P3 remain (block 116); therefrom the smallest value must be determined. This will be the next to the smallest value of the four image values P1 ... P4. The determination of this value is performed as follows.

In block 117 P1 is compared with P2. When P1 is smaller than P2, a branch operation takes place to block 118 in which P1 and P3 are compared. When P1 is again smaller than P3, P1 is stored as the smallest image value (block 119) and otherwise P3 is stored (block 120). However, if the comparison in block 117 reveals that P1 is not smaller than P2, a branch operation takes place to block 121 in which P2 and P3 are compared. If P2 is not larger than P3, P2 is stored as being the smallest one of the three image values (block 122), and otherwise P3 is stored. After completion of these two further comparisons (117 and 118 or 117 and 121) it is thus known which one is the smallest of the three remaining image values and hence the next to the smallest one of the total of four image values P1 ... P4 (block 123). This value is used as the image value of the layer image point. This operation is repeated for all layer image points until a layer image has been formed from the four single images.

Subsequently, the same single images can be used in order to form layer images which represent a layer which is situated deeper or higher in the object. However, it is also possible to use four single images which represent the coronary vessels in a different phase of the cardiac cycle to form one or more layer images.

Even though the invention has been described with reference to a version where the mask image is derived from X-ray filled images, the invention can also be used for subtraction methods where the mask image is derived in a different manner, for example as described in the magazine "Radiology", Vol. 151, No. 2, Pages 517 to 520.

Moreover, the invention can be used not only for methods where the single images are derived from the X-ray images by means of a subtraction method, but also for methods where the single images are derived from the X-ray images by means of a pattern enhancement method. As a result, faults in objects, for example shrinkholes in cast products, can be recognized and the errors in individual image points of the single images, introduced by the pattern recognition method, can be substantially eliminated by formation of the layer image.

What is claimed is:

1. In a method for generating for X-ray layer images of an examination zone of the type comprising the steps of generating a plurality of different projection images of the examination zone, each of said projection images being generated from a different perspective and being represented as image values for a plurality of image points, and combining the values for corresponding image points in the projection images to generate a value for each point in a layer image; the improvement wherein the step of combining the values comprises choosing the next to the lowest value from the values of the corresponding image points in the projection images to be the value of the corresponding image point in the layer image.

2. The method of claim 1, for medical x-ray diagnosis, wherein the projection images are formed by subtracting mask images from images of blood vessels which are filled with a contrast medium.

3. The method of claim 2 wherein the values of image points in the projection images are processed to enhance features therein.

4. In a device which generates x-ray layer images, of the type comprising means for projecting x-rays through an examination zone from a plurality of spatially diverse source points to produce projection images of the examination zone from the plurality of distinct perspectives and means for combining corresponding points in each of the projection images to form a single layer image, the improvement wherein the means for combining comprises means which store corresponding image point values from each of the projection images and which select, from the values of corresponding points in each of the projection images, the next to the lowest of said values for use as the value at a corresponding point in the layer image.

5. The device of claim 4 further comprising pattern enhancement means which modify the values at image points in the projection images to enhance features therein.

* * * * *